United States Patent [19]

Steinman et al.

[11] Patent Number: 5,000,952

[45] Date of Patent: Mar. 19, 1991

[54] POLYPEPTIDE PERTUSSIS TOXIN VACCINE

[75] Inventors: Lawrence Steinman; Jorge R. Oksenberg; Gary K. Schoolnik, all of Palo Alto; Amrit K. Judd, Belmont, all of Calif.

[73] Assignee: The Board of Trustees of the Leland Stanford, Jr. University, Stanford, Calif.

[21] Appl. No.: 227,372

[22] Filed: Aug. 2, 1988

[51] Int. Cl.$^5$ ............................................. A61K 39/10
[52] U.S. Cl. ..................................... 424/92; 530/327; 435/252.5
[58] Field of Search ........................... 424/92; 530/327

[56] References Cited

U.S. PATENT DOCUMENTS 4,338,299 7/1982 Vesselinova et al. ................. 424/92
4,857,318 8/1989 Lee ....................................... 424/92

OTHER PUBLICATIONS

Steinman et al., CA 113(5) Abst. No. 38746n, (1989).

Oksenberg et al., J. Immunol., 143(12), pp. 4227–4231, (1989).

DeMagistris et al., J. Exp. Med., 169(5), pp. 1519–1532, (1989).

Primary Examiner—David B. Springer
Attorney, Agent, or Firm—Bertram I. Rowland

[57] ABSTRACT

A novel method of defining oligopeptides is provided for determining useful immunodominant sequences for use as vaccines for pathogens. The method involves identifying sequences by particular selection procedures and using such sequences with antigen-presenting cells and T-cells to demonstrate activation of the common histocompatibility antigens DQ and DR in humans and their analogs in other animals. The oligopeptides may then be used individually or in combination to produce safe and effective vaccines, where genes may be prepared encoding the oligopeptides and used for expression of the oligopeptides or combinations of the oligopeptides or the gene transformed into the appropriate host, e.g., *B. pertussis*, for use as a vaccine to the intact organism.

10 Claims, No Drawings

POLYPEPTIDE PERTUSSIS TOXIN VACCINE

This invention was supported in part by a grant from the NIH (ROI Al 22462). The U.S. government may have rights.

TECHNICAL FIELD

The subject invention concerns the design of peptide vaccines other than intact antigens.

BACKGROUND

Vaccines have depended to a great degree on substantially intact organisms. By using substantially intact organisms which were attenuated or killed, it was hoped that one could reproduce the native pathogen conformation and immune response, so that the immune system would be activated and create memory cells without having to be subjected to the pathogenicity of the virulent organism. For some diseases this has proven quite satisfactory. However, in other cases, the method has failed for a variety of reasons.

When using live, attenuated organisms, there is always the concern that the attenuated organism may be restored to virulency. While in individual cases, the probability is low, where one is doing mass vaccinations, having a pathogenic organism greatly increases the likelihood of infection among a few patients. In other instances, toxins may be involved, which to varying degrees in individuals may result in disease symptoms. In these situations one must weigh the beneficial effects for the major population against the adverse effects to individuals. The situation applies to whooping cough, caused by the organism *Bordetella pertussis*. The *pertussis* toxin is an enzyme which catalyzes ADP-ribosylation. The toxin has a broad spectrum of adverse effects on the host. Thus in the case of the vaccine, it is not sufficient that the organism be inactivated since the intact toxin can provide for life-threatening results.

Based on various investigations, it is believed today that different individuals may respond to different portions of an antigen. In the case of antigen-presenting cells such as B-cells, one protein may bind to the surface immunoglobulin and another protein may bind to an MHC antigen and be presented to and recognized by T-cells. Thus in humans, depending on the HLA-type, the response to an antigen may vary between different individuals, and some individuals may not mount a strong immmune response to the antigen.

There is therefore substantial interest in being able to develop vaccines which will have broad application throughout the population without the uncertainties of using either attenuated or killed intact pathogens, while providing for a strong immune response in all or substantially all individuals to be vaccinated.

RELEVANT LITERATURE

Tamura et al., Biochemistry (1982) 22:5516 describes the various subunits of the *pertussis* toxin. Locht and Keith, *Science* (1986) 232:1258; and Nicosia et al., *Proc. Natl. Acad. Sci. (USA)* (1986) 83:4631 describe the cloning and sequencing of the subunits of the pertussis toxin. Heffron, et al., *Proc. Natl. Acad. Sci. (USA)* (1978) 75:6012; Black and Falkow, *Infect. Immun.* (1987) 55:2465; and Stibitz et al., *Gene*, (1986) 50:133 describe the mutagenesis of the S1 subunit of the *pertussis* toxin. Black et al., *Science* (1988) 240:656 describe the testing of a mutagenized S1 subunit as a toxin and vaccine. DeLisi and Berzofsky, *Proc. Natl. Acad. Sci. (USA)* (1985) 82:7048; Hopp and Woods, *Proc. Natl. Acad. Sci. USA* (1981) 78:3824; Chou and Fasman, Adv. Enzymology (1978) 47:45; and Rothbard and Taylor, *Embo. J.* (1988) 7:93 describe methods of determining immunodominant sites in a protein sequence. Zamvil et al., Nature (1986) 324:258; and Brocke et al. (1988) *J. Clin. Investigation* (in press) describe the application of the Rothbard algorithm to experimental allergic encephalomyelitis and myasthenia gravis. Bannerjee et al., *J. Exp. Med.* (1988) 167:832 describe the possible role of V$\beta$T cell receptor genes in susceptibility to collagen-induced arthritis in mice. Burnette et al., Biotechnology (1988) 6:699 and Bartoloni et al., Biotechnology (1988) 6:709 describe the *pertussis* toxin.

SUMMARY OF THE INVENTION

Methods and compositions are provided for the determination of peptide sequences in a protein of a pathogen, which sequences may be employed in a vaccine. The method employs selecting sequences in conjunction with syngeneic and/or allogeneic cells. The method and compositions find exemplification with the S1 subunit of the *pertussis* toxin.

DESCRIPTION OF THE SPECIFIC EMBODIMENTS

Methods and compositions are provided for devising vaccines based on sequences present in antigenic proteins of pathogens. The methods provide for selection of sequences which allow for a reasonably high probability of being immunodominant sequences, while avoiding the need to prepare fragments which overlap the entire molecule. They may be further selected by employing combinations of syngeneic and/or allogeneic antigen-presenting cells, macrophage or B-cell, in combination with T-cells, particularly helper cells (CD4+). By selecting for the more common HLA types in humans and the more common MHC types in other animals, particularly domestic animals, one may select for those sequences which bind to the common histocompatability antigens. Frequently, correlations exist between human histocompatability antigens and the antigens of other animals, so that screening may be performed with animal cells, e.g. mouse or non-human primate cells. In this manner, with a few oligopeptides one can cover substantially all of the population to be vaccinated and produce an immune response.

Various screening techniques may be employed, particularly cell proliferation as a result of activation by binding between the antigen-presenting cell and the T-cell. Once the activation has been demonstrated, the oligopeptide may be used by itself or in conjunction with the other oligopeptides, either combined covalently or non-covalently to provide for an immune response. The compositions may then be formulated in conventional ways for administration as a vaccine or to produce antibodies to the pathogen antigen.

The subject method will be exemplified with the *pertussis* toxin. The *pertussis* toxin is a particularly good example, since the intact subunit S1 of the *pertussis* toxin is believed to be capable of producing various adverse effects on the vaccinated host. The S1 subunit is capable of ADP-ribosylation and may be involved with hypotonic, hyporesponsive syndrome, convulsions and encephalopathy. Thus the intact antigen is a serious health concern for a broadly applicable vaccine.

In carrying out the subject invention, the antigen sequence is screened for one or both of the following entities:

The first analysis is selection of regions of high flexibility, including the regions of predicted B-turns (Chou and Fasman, supra; Hopp and Woods, supra); amino acids associated with the termini of helices; and of amphipathic helices as part of the secondary structure of the antigen, as described by DeLisi and Berzofsky, supra. By drawing a helix where the majority of amino acids facing or generally directed in one direction are substantially hydrophobic, while the majority of amino acids facing or generally directed in the opposite direction are substantially hydrophilic, that sequence has a reasonable probability of being an immunodominant sequence, in that it binds to a histocompatibility antigen. By selecting regions of high flexibility, linear sequences are most likely to elicit both T- and B-cell responses. T- and B-cell epitopes may overlap (Manca et al., *Eur. J. Imm.* (1985) 15:345) and such overlapping epitopes may be preferred vaccines due to their high immunogenicity.

The second analysis looks for a charged residue or a glycine followed by two hydrophobic residues in either structure, while the remainder were selected by the Rothbard algorithm. It should be noted that in each of the Rothbard sequences, the first amino acid is glycine or a charged amino acid, in the present situation particularly arginine.

The sequences may then be screened for their ability to stimulate antigen-presenting cells (APC's) when the APC's are combined with matched T-helper cells—i.e., T-cells restricted by the APC's. Where the T-helper cells may be syngeneric, semi-syngeneric or allogeneic. The T-cells should share at least one common histocompatibility antigen with the APC. With S1, it is found that HLA-DP does not appear to be involved, while the HLA-DR and/or DQ determinants are involved.

The screening with syngeneic APC's and T-cells allows for detection of one or more histocompatibility antigens which bind the particular oligopeptide, but is limited to the particular T-cell genotype of the host source. By employing allogeneic T-cells having at least one common histocompatibility type with the antigen-presenting cell, one can further screen as to the generality of the T-cell genotype for detecting and responding to the particular peptide.

TABLE 1

Pertussis Toxin (Subunit 1) Peptides Used for T-Cell Stimulation

| Residues | |
|---|---|
| 44–54 | NH$_2$—Arg—Tyr—Asp—Ser—Arg—Pro—Pro—Glu—Asp—Val—Phe—COOH |
| 64–75 | NH$_2$—Asp—Asn—Val—Leu—Asp—His—Leu—Thr—Gly—Arg—Ser—Cys—COOH |
| 87–98 | NH$_2$—Thr—Ser—Ser—Ser—Arg—Arg—Tyr—Thr—Glu—Val—Tyr—Leu—COOH |
| 104–116 | NH$_2$—Glu—Ala—Val—Glu—Ala—Gly—Arg—Ala—Gly—Arg—Gly—Thr—Gly—COOH |
| 206–218 | NH$_2$—Arg—Ala—Asn—Pro—Asn—Pro—Tyr—Thr—Ser—Arg—Arg—Ser—Val—COOH |
| 133–146 | NH$_2$—Gly—Ala—Ala—Ser—Ser—Tyr—Phe—Glu—Tyr—Val—Asp—Thr—Tyr—Gly—COOH |
| 151–161 | NH$_2$—Arg—Ile—Leu—Ala—Gly—Ala—Leu—Ala—Thr—Tyr—Gln—COOH |
| 169–179 | NH$_2$—Arg—Ile—Pro—Pro—Glu—Asn—Ile—Arg—Arg—Val—Thr—COOH |
| 180–190 | NH$_2$—Arg—Val—Tyr—His—Asn—Gly—Ile—Thr—Gly—Glu—Thr—COOH |
| 223–233 | NH$_2$—Gly—Thr—Leu—Val—Arg—Met—Ala—Pro—Val—Ile—Gly—COOH | direction, namely N-C or C-N. Rothbard and Taylor, supra. Sequences are selected which incorporate the oligopeptide sequence fulfilling the above objectives.

Generally, the sequence will be at least 8 amino acids, preferably 9 amino acids, more preferably 10 amino acids, and usually not exceeding 20, more usually not exceeding 18 amino acids, as the functional entity. Of course, longer sequences may be employed, particularly where there are adjacent or overlapping immunodominant sequences or where the longer sequence provides for some advantage in synthesis, stability, or the like. The defined oligopeptide sequence may be at the N-terminus, C-terminus, or internal to the oligopeptide sequence, while the Rothbard algorithm will usually be located proximal to or at the N-terminus of the oligopeptide. Usually, the peptides screened will have at least about 10 amino acids and at least 80% of such sequence will be used in a vaccine.

For the most part the sequences will be of high flexibility and either at the N-terminus of the protein or regions of predicted β-turns. In many situations, the two methods of selection will not provide for overlapping sequences and the sequences selected by the two methods will each be tested. Usually, at least 20%, preferably at least about 25% of the selected sequences will prove to be useful as immunodominant sequences with one or more of the common histocompatibility antigens.

In the case of *pertussis* toxin subunit 1 (S1), the oligopeptides which were selected are set forth in Table 1, where the first five were selected by the secondary Besides evaluating with a method of providing a positive response, one may also look to the reversal of the response in conjunction with antibodies to the histocompatibility antigen. Thus, where there is a reversal of the proliferative activity in relation to an antibody specific for one of the histocompatibility antigens present, this indicates that at least that histocompatibility antigen is involved with the presentation of the oligopeptide. In this way, one can map which specific histocompatibility antigen presents which oligopeptide. Since the common histocompatibility antigens are known, particularly for humans and these have been correlated with the mouse MHC antigens, antigen-presenting cells having these histocompatibility antigens may be employed and the specific histocompatibility involved with proliferative response determined by demonstrating reversal with antibody. The result is further confirmed by the absence of reversal for antibody binding to other histocompatibility antigens present in the proliferation test.

For *pertussis* toxin, sequences of specific interest include 64–75 and 151–161.

The sequences may be used in a variety of ways. Since, for the most part, oligopeptides are not antigenic, the oligopeptide sequence will normally be employed in conjunction with antigens and/or adjuvants. For the purposes of the subject invention, the desired oligopeptides may be linked together to form a polypeptide of at least about 30 amino acids, preferably at least about 60 amino acids, where the oligopeptides may be joined directly or through a linking chain, or joined to a protein or protein fragment which is known to enhance the antigenic response. Where the oligopeptides are linked together, they will usually be free of naturally occurring intervening sequences. In addition, small oligopeptides will normally have very short half-lives when administered as a vaccine. It is therefore necessary to provide means for stabilizing the lifetime of the oligopeptide to provide for binding to the antigen-presenting cell.

Stabilization of the oligopeptide may be achieved in a variety of ways. One method, as already indicated, is to prepare a large polypeptide using sequences other than the selected oligopeptide sequences to provide for stabilization. Alternatively, the oligopeptide sequences of interest may be introduced into liposomes or other vesicles, bound to particles or substrates which allow for ingestion by APC's, while substantially reducing the probability of digestion by proteases. D-isomer amino acids may be included in the oligopeptide, particularly outside the binding helix. The termini may be functionalized or an amino acid side group modified in order to modify a proteolytically sensitive site. Thus the subject oligopeptides may be joined together to form a single protein or mixture of proteins, or may be used individually or in combination by employing various procedures which allow for protection of the oligopeptides without interfering with their activation of the immune response or, preferably, enhancing the immune response.

The oligopeptides of the subject invention may be prepared in a variety of ways. For those oligopeptide compositions, where the same or different oligopeptides are combined in a single polypeptide, by themselves or in conjunction with other polypeptides, and the molecule has fewer than about 60 amino acids, the compositions may be synthesized. Commercial synthetic apparatuses are available for use and may be used with advantage. However, for the most part, for polypeptides of greater than about 30 amino acids, genetic engineering may be used, where a gene may be synthesized or prepared by a combination of synthetic sequences and natural sequences. For the most part, the peptides which are employed will be less than about 600,000 molecular weight, preferably less than about 300,000 molecular weight, and more preferably less than about 200,000 molecular weight. Usually the peptide will comprise less than about 50 number percent of the amino acids of the intact pathogen polypeptide or subunit, so that usually only a small portion, usually about 25% or less of the naturally occuring protein will be employed. Thus sequences may be designed comprising about 2 knt or fewer, preferably about 1 knt or fewer, and more preferably 0.5 knt or fewer.

The resulting gene may then be used to express the desired polypeptide in an appropriate host. A large number of expression vectors are available today, which can be used in a variety of unicellular hosts, both prokaryotic and eukaryotic. In this manner the protein can be prepared where it will be produced intracellularly in such organisms as *E. coli, Bacillus subtilis* or other bacillus organisms, yeast such as *Sacchromyces cerevisiae* or other yeast, or the like. Desirably, the gene may be substituted for a S1 gene in *B. pertussis*. In this manner, a live or killed vaccine may be employed which lacks the S1 subunit, but includes the desired oligopeptide sequences for initiating a neutralizing immune response. Furthermore, not only will the host be immunized against the proteins of the target pathogen, but the host will also be immunized against the *pertussis* toxin.

Methods for providing a host organism having a polypeptide according to this invention and lacking a functional S1 subunit find analogy in the literature. One may select for a *B. pertussis* host which lacks a functioning S1 protein and transform such host with an expression vector comprising a subject polypeptide and a DNA sequence of at least about 50 bp homologous with a non-essential sequence of the host chromosome. In this way, recombination may occur whereby the subject polypeptide will become integrated into the chromosome. Expression of the subject polypeptide may then be determined by a Western blot, while integration may be determined by fragmentation of the chromosome and detecting hybridization with an appropriate probe. Conveniently, a vector may be employed which is unstable in the host and will be lost but carries antibiotic resistance or provides phototrophy to an auxotrophic host. In this manner, by selecting for hosts which retain the selected marker, such hosts have a high probability of also retaining the subject gene encoding the immunogenic polypeptide integrated into the chromosome.

Alternatively, one may provide for recombination between the *pertussis* toxin S1 subunit gene and the gene encoding the subject oligopeptide by employing the untranslated 5' and 3' sequences of the S1 subunit gene as boundaries for the subject gene. One would then screen for hosts which no longer have the wild-type toxin gene, but have substituted the subject gene instead.

For expression of the subject polypeptides, an expression cassette is employed where one employs a promoter or transcriptional initiation region functional in the expression host. For the subject invention, one will normally employ a strong promoter, where the promoter will be associated with a protein produced at at least a relatively high level in the host, or a virus or phage promoter which is functional in the host. The promoter may be inducible or constitutive, usually depending on whether the host will be the vaccine; whether, if the host is used as a vaccine, the host is live or dead; whether the protein is to be harvested and used as a vaccine extracellularly.

A wide variety of promoters are available for use in bacteria, including Bordetella, which include the lac, trp, tac, $\pi$ left and right promoters, omp, T7, early or late promoters, etc. Of course, one could also use the S1 wild-type promoter.

Downstream from the promoter in the direction of transcription will be the subject gene, followed by the terminator sequence which allows for termination, which terminator sequence is functional in the selected host. A wide variety of terminator sequences are known and have been used and do not require description here. In many instances, expression cassettes are readily available where the promoter and terminator are separated by a polylinker and already exist in a vector which is capable of stable or unstable replication in the particular host and may include one or more markers for selection of the host. Where such vectors are available, after synthesizing or preparing the subject gene, the gene may be provided with blunt ends or linkers and be directly inserted into the polylinker to be under the transcriptional control of the promoter.

The genes which are prepared will encode at least one of the subject oligopeptides and, desirably, two or more, usually not more than 10, usually not more than 6.

Each of the oligopeptides may be present in one or more copies, usually not more than about 10, usually not more than about 6. Where synthesized, one may employ codons which are preferred by the particular host so as to enhance the rate of expression, avoiding limitations associated with low levels of the particular tRNA.

Depending upon the nature of the particular vaccine, it may be formulated in a variety of ways. As already indicated, the polypeptides may be formulated as liposomes, bound particles, or as present in a live or dead host. Various adjuvants may be employed, such as aluminum hydroxide, oils, complex saccharides, liposaccharides, or the like. The amount of the vaccine will vary depending upon its nature, generally being from about 1 μg to 1 mg/kg host, more usually from about 20 to 500, μg/kg of host and administered in an amount of about 0.25 to 2 ml, more usually 0.5 to 1 ml. Various physiologically acceptable carriers may be employed such as water, alcohol, phosphate buffered saline or the like. One or more administrations may be employed, where the administrations may be oral, parenterally by injection (e.g., subcutaneously intramuscularly, intravenously, etc), etc.

The subject oligopeptides may be used by themselves or in combination with sequences from other pathogens. Thus a single polypeptide may include not only the immunodominant sequences from the S1 toxin, but also immunodominant sequences from other pathogens, so as to provide a combined vaccine. The polypeptides which are employed may be mixtures of polypeptides or a single polypeptide employing the various polypeptide sequences. Various pathogens of interest which may provide oligopeptide sequences include Rubella, smallpox, diphtheria, varicella, HIV-1 and -2, etc.

The following examples are offered by way of illustration and not by way of limitation.

MATERIALS AND METHODS

Synthetic peptides

Peptides were synthesized by a solid phase technique starting with commercially available t-Boc amino acid polystyrene resin and t-Boc protected amino acids with the following side-chain protecting groups: O-benzyl esters for Asp and Glu, O-benzyl ethers for Ser and Thr, tosyl for Arg and His, p-methoxybenzyl for Cys, ortho-chlorobenzyloxycarbonyl for Lys, and 2,6-dichlorobenzyl for Tyr. All couplings were performed using 2.5 molar excess of t-Boc amino acid and dicyclohexylcarbodiimide (DCC) over the number of milliequivalents of amino acid on the resin. In the case of Asn and Gln, a 2.5 molar excess of N-hydroxybenzotriazole (HOBI) was added. If the peptides had His in their sequence, then for Asn and Gln, active ester (p-nitrophenyl) couplings were performed. All the couplings were monitored by the ninhydrin test. 40% trifluoroacetic acid/dichloromethane containing 0.1% indole was used for Boc deprotection. After synthesis, the peptides were cleaved from the resin using anhydrous HF in HF Reaction Apparatus Type II (Peninsula Labs). The peptides were separated from the various organic side products by extraction with ether and isolated from the resin by extraction with 50% acetic acid, diluted and lyophilized. Crude peptides were purified by gel filtration on Sephadex LH-20. Purity of the peptides was checked by analytical reverse phase HPLC and amino acid analysis.

Subjects

Peripheral blood lymphocytes (PBL) of healthy adult volunteers previously immunized with the whole cell *B. pertussis* vaccine, were isolated by centrifugation over Histopaque gradients (Sigma, St. Louis, Mo.). HLA-DR, DQ typing was performed on nylon wool T cell depleted, B cell enriched lymphocytes by the NIH standard complement-dependent extended microcytotoxicity technique.

Proliferation assay

PBL from HLA-DR, DQ typed donors were cultured with different concentrations of the synthetic peptides in round bottom microtiter plates at a concentration of $2\times10^5$ cells in 0.2 ml of culture medium. Culture medium was composed of RPMI 1640 (Mediatech, Washington, D.C.) supplemented with 20% heat inactivated pooled human serum (Irvine Scientific, Santa Ana, Calif.), 2 mM L-glutamine and antibiotics. After 72 h, cultures were pulsed with [$^3$H] thymidine (1 μCi/well, specific activity 5 Ci/mmole). 18 h later, the cells were harvested and thymidine incorporation was measured in a liquid scintillation counter.

Preparation of antigen presenting cells and T lymphocytes

Antigen presenting cells (APC's) were prepared from PBL as described by Freundlich and Avdalovic, *J. Immunol Methods* (1983) 62:31. Briefly, the method involves the incubation for 120 min and adherence of cells bearing receptors for fibronectin to plastic petri dishes coated with gelatin and autologous plasma. An enriched T lymphoctye population was obtained by passage of the fibronectin nonadherent cells through a nylon wool column. Using a panel of monoclonal antibodies, it was shown that the fibronectin adherent cells are positive for HLA class I and class II antigens and do not express T cell markers (Oksenberg, et al., *Am. J. Reprod. Immunol. Microbiol.* (1986) 11:82).

Antibody blocking experiments

Fibronectin adherent APC's or non adherent T cells were incubated for 60 minutes with various concentrations of the different monoclonal antibodies (mAb). Cells were extensively washed before co-culture. Blocking was determined by the percent of the response obtained in the presence of antigen plus mAb, divided by the response with antigen alone. The following mAb were used: L243, and anti HLA-DR (mouse IgG2a) reactive with a monomorphic HLA-DR epitope; SK10, and HLA-DQ (Leu 10) (mouse IgG1), which recognizes a common polymorphic epitope on DQw 1 and DQw 3 molecules; B7/21, an anti HLA-DP (mouse IgG1,) which recognizes a monomorphic epitope present on DP molecules of cells expressing DP1, DP2, DP3, DP4 or DP5 and anti CD4 (Leu 3a) (Becton-Dickinson, Mountain View, Calif.). Polyclonal rabbit anti pertussis toxin was obtained by consecutive injection of PT (Islet Activating Protein, List Biological Laboratories, Campbell, Calif.) in complete Freund's adjuvant. Rabbits were injected intramuscularly with 3 ml of the emulsified antigen (200 ng/ml). Immunization was repeated after one month, and rabbits were bled 2 weeks later. The boosting and bleeding cycle was repeated after a 3 week resting period.

Bromodeoxyuridine and light treatment

Responder lymphocytes ($10\times10^6$/flask) and X-irradiated stimulator lymphocytes ($10\times10^6$/flask) were cocultured at 37° C., 5% $CO_2$ in 20 ml of culture medium. Two μg/ml of 5-bromo-2-deoxyuridine (Brd Urd, Sigma, St. Louis, Mo.) were added to the cultures at 48 h. At 17 h, the cultures were illuminated for 180 min. by a fluorescent light source to eliminate alloreactive clones (Janeway and Paul, J. Exp. Med. (1976)

144:1641). This procedure diminished the specific allogeneic response by about 75-85%. The surviving clones were then incubated with peptide primed APC to test genetic restriction. It should be noted that the ability of these cells to respond to PHA and non-relevant allogeneic stimulation was not compromised by the treatment.

Results

Based on the algorithm of DeLisi and Berzofsky employing secondary structure and the algorithm of Rothbard based on amino acid sequence the following residues were selected. For secondary structure, residues 44-54, 64-75, 87-98, 104-116, and 206-218. For the algorithm sequence, residues 133-146, 151-161, 169-179, 180-190, and 223-233 were selected. Healthy adult volunteers previously immunized with *pertussis* vaccine as children were tested. A representative-dose response experience is one in which PBL of donor JO (HLA-DR 3, 8; DQw2) responded to 3 of the 5 peptides selected by the first algorithm and 2 of the 5 peptides selected by the Rothbard algorithm. Individual responses to various peptides differed markedly. Each individual could be stimulated by more than one peptide, but none of the peptides elicited response in the entire panel of responders. However, it was possible to show that by the combination of two peptides, p64-75 and p151-161, it was possible to cover the entire respondent panel. The table on the following page indicates the results. Lymphocytes of the different responders stimulated with the peptides respond vigorously to a second challenge with *pertussis* toxin, suggesting that suppressor cells were not indicated in the non-responsiveness. Because individuals who shared HLA genotypes may not be expected to share T-cell receptor genotypes, it was not totally unexpected that individuals sharing the same HLA genotype might not respond in the same way to a panel of oligopeptides (Bannerjee et al., supra). Individuals sharing the HLA-DR2,5 genotype responded to p44-54 and p133-146, but did not both respond to p64-75, p87-98, p151-161, p169-179 and p223-233.

In order to analyze the role of HLA molecules in response to *pertussis* toxin (PT) peptides, two different approaches were employed: Blockade of a response to a given peptide with monoclonal antibodies (mAb) directed to HLA-D molecules and use of HLA-D matched APC's for presentation of peptides to heterologous purified T-cells. With three different individuals, presentation of peptides p44-54, p104-116, p206-218, p133-146, p151-161, and p223-233 by fibronectin adherent APC's was largely inhibited by the anti-HLA-DR mAb, while anti-HLA-DQ was only able to suppress certain responses by about 10 to 20%. Leu10 mAb (anti-HLA-DQw1, w3) blocked the responses to peptides 64-75, 87-98 and 169-179, while the anti-HLA-DR mAb was associated with a much smaller reduction in the response to these peptides. Treatment of APC's with anti HLA-DP or control with anti-PT antibodies caused only marginal reductions in the responses. These results support the conclusion that the different epitopes of the PT molecule associate with either HLA-DR or DQ determinants. Antibody-blocking studies showed that peptide stimulation could be blocked by treatment of non-adherent lymphocytes with anti-CD4 but not anti-HLA Class II mAb.

TABLE 2*

| Peptides | HLA-DR | | | | | | | | |
|---|---|---|---|---|---|---|---|---|---|
| | 1,- | 1,4 | 2,4 | 2,5 | 2,5 | 3,w8 | 5,w8 | 5,7 | w6,7 |
| 44-54 | H | N | N | H | H | H | L | H | H |
| 64-75 | H | N | N | N | H | H | H | H | N |
| 87-98 | H | N | H | N | I | H | H | L | N |
| 104-116 | H | I | I | N | N | N | H | H | N |
| 206-218 | N | N | N | N | N | N | H | N | N |
| 133-146 | N | H | H | L | L | N | N | N | H |
| 151-161 | H | I | H | I | N | H | N | H | H |
| 169-179 | H | N | H | N | I | H | H | N | N |
| 180-190 | N | N | N | N | N | N | N | N | N |
| 223-233 | N | H | H | N | I | N | N | N | H |
| 64-75/ 151-161 | H | I | H | Z | H | H | I | H | H |

*Lymphocyte proliferative indices from nine normal HLA-DR typed individuals to the Pertussis toxin (PT) peptides at 2, 5, 10, 20 and 100 μg/l. Results are given for the peptide concentration that elicited the greatest proliferation which was usually 10 or 20 μg/ml. Background cpm (no peptide) ranged from 150 to 2500 cpm. High responders (H) (SI > 15); intermediate responders (I) (SI > 6 and < 15); low responders (L) (SI > 3 and < 6); and nonresponders (N) (SI < 3).

The second experimental approach involved use of heterologous APC's and T-cells which differ or share HLA-DR, DQ determinants. Alloreactive T-cell clones were activated by Brd Urd and light treatment, eliminating irrelevant proliferative reactions.

As shown in Table 3, only combinations in which the APC's shared HLA Class II antigens with the respondent T-cells resulted in significant peptide responses. Results support the critical role of the T-cell repertoire in the peptideresponses. Combinations of a "non-responder" APC and "responder" T-cells gave positive responses, while "responder" APC's and "non-responder" T-cells yielded negative responses. For example, HLA-DR 2,4; DQw1, w3 APC's effectively presented p104-116, p133-146, p151-161, p169-179 and p223-233 to HLA-DR 1,4; DQ w1, w3 T-cells. The individual who was HLA-DR2 4; DQ w1, w3, responded to p87-98 and p169-179, as well as p104-116, p133-146, p151-161 and p223-233. However, the HLA-DR 2,4; DQ w1, w3 APC's could not effectively present p87-98 or p169-179 to the T-cells of an HLA-DR 1,4; DQ w1, w3, individual who was a non-responder to these peptides. A similar pattern was seen with HLA-DR 5,7 APC's and HLA-DR w6, 7 T-cells where responses were effectively mounted to p44-54, p133-146, p151-161 and p223-233, but not to p64-74 and p104-116, which effectively stimulated the donor of the APC's but not the donor of the T-cells.

The above data demonstrate that one can produce oligopeptides which are effective in producing an immune response to *pertussis* toxin without requiring the complete antigen which may have adverse physiological effects on a human host. The subject peptides can be combined for activation of the immune system in a wide variety of HLA-APC's, so that by employing polypeptides which are effective for the most common histocompatibility antigens, one can ensure an

TABLE 3

MHC restriction and T cell reactivity after Brd Urd and light treatment.

| | *T-Cells | | | | | | | |
|---|---|---|---|---|---|---|---|---|
| | APC's HLA-DR2,4; DQw1,w3 | | | | APC's HLA-DR 5,7; DQw2,w3 | | | |
| Peptides | HLA-DR 1,4 DQw1,w2 | | HLA-DR 3,w8 DQw2 | | HLA-DR 6,7 DQw1,w2 | | HLA-DR1, DQW1 | |
| 44-53 | 1260 | 0.95§ | 1670 | 1.05 | 12830 | 4.48 | 2910 | 1.71 |
| 64-75 | 1230 | 1.04 | 2560 | 0.67 | 725 | 0.69 | 3860 | 1.54 |
| 87-98 | 1920 | 0.83 | 1880 | 1.89 | 854 | 0.64 | 1910 | 1.59 |
| 104-116 | 16730 | 5.46 | 2960 | 1.27 | 710 | 1.01 | 660 | 0.67 |
| 206-218 | 1870 | 1.80 | 2490 | 1.24 | 530 | 0.47 | 960 | 1.77 |
| 133-146 | 31125 | 12.20 | 860 | 0.77 | 24860 | 8.63 | 3820 | 2.74 |
| 151-161 | 9920 | 11.40 | 1780 | 0.89 | 25330 | 8.40 | 4190 | 1.63 |
| 169-179 | 4010 | 5.07 | 2280 | 1.78 | 830 | 0.77 | 750 | 0.96 |
| 180-190 | 1210 | 1.07 | 1975 | 2.29 | 1930 | 1.94 | 920 | 0.87 |
| 223-233 | 22860 | 11.72 | 3320 | 1.44 | 48960 | 13.19 | 1970 | 1.28 |

*Purified T lymphocytes after Brd Urd and light treatment subsequently stimulated with peptide primed heterologous APC's.

Counts per minute. Each value represents the mean of two different triplicate determinations. Standard deviation values never exceeded the 12% of mean cpm.

$$\S\text{Stimulation Index} = \frac{\text{Experimental cpm(+antigen)}}{\text{Control cpm(−antigen)}}$$

effective response throughout the population. Conveniently, genes may be prepared which encode the subject oligopeptides, where the genes may be used in expression vectors for production of novel polypeptides or the gene may be transformed into the *B. pertussis* host which is negative for active toxin or is made so by the transformation. In this manner, effective vaccines may be produced without occurrence of adverse effects in a small but significant portion of large populations treated with a vaccine.

Although the foregoing invention has been described in some detail by way of illustration and example for purposes of clarity of understanding, it will be obvious that changes and modifications may be practiced within the scope of the appended claims.

What is claimed is:

1. A polypeptide useful as a *B. pertussis* vaccine comprising at least one oligopeptide comprising at least about 80% of at least one of the following sequences of the S1 subunit which are substantially free of intervening amino acid sequences of the S1 subunit wherein the sequence 44-54, 64-75, 87-98, 104-116, 206-218, 133-146, 151-161, 169-179, 180-190, and 223-233,

| | |
|---|---|
| 44-54 | $NH_2$—Arg—Tyr—Asp—Ser—Arg—Pro—Pro—Glu—Asp—Val—Phe—COOH |
| 64-75 | $NH_2$—Asp—Asn—Val—Leu—Asp—His—Leu—Thr—Gly—Arg—Ser—Cys—COOH |
| 87-98 | $NH_2$—Thr—Ser—Ser—Ser—Arg—Arg—Tyr—Thr—Glu—Val—Tyr—Leu—COOH |
| 104-116 | $NH_2$—Glu—Ala—Val—Glu—Ala—Glu—Arg—Ala—Gly—Arg—Gly—Thr—Gly—COOH |
| 206-218 | $NH_2$—Arg—Ala—Asn—Pro—Asn—Pro—Tyr—Thr—Ser—Arg—Arg—Ser—Val—COOH |
| 133-146 | $NH_2$—Gly—Ala—Ala—Ser—Ser—Tyr—Phe—Glu—Tyr—Val—Asp—Thr—Tyr—Gly—COOH |
| 151-161 | $NH_2$—Arg—Ile—Leu—Ala—Gly—Ala—Leu—Ala—Thr—Tyr—Gln—COOH |
| 169-179 | $NH_2$—Arg—Ile—Pro—Pro—Glu—Asn—Ile—Arg—Arg—Val—Thr—COOH |
| 180-190 | $NH_2$—Arg—Val—Tyr—His—Asn—Gly—Ile—Thr—Gly—Glu—Thr—COOH |
| 223-233 | $NH_2$—Gly—Thr—Leu—Val—Arg—Met—Ala—Pro—Val—Ile—Gly—COOH. |

2. A polypeptide according to claim 1, comprising at least 80% of at least one of the sequences 64-75 and 151-161.

3. A polypeptide according to claim 2, wherein all of both of said sequences are present.

4. A polypeptide according to claim 2, wherein said polypeptide further comprises an immunogen for a human host.

5. A polypeptide according to claim 4, wherein said polypeptide is less than about 600 kdaltons.

6. A vaccine composition comprising a polypeptide according to claim 1 in an amount sufficient to produce an immune response in a human host in a physiologically acceptable carrier.

7. A vaccine composition according to claim 6, wherein said composition further comprises an adjuvant to enhance the immune response.

8. A vaccine composition according to claim 6, wherein said polypeptide comprises at least 80% of at least one of the sequences 64-75 and 151-161.

9. A method for protecting a human host against whooping cough which comprises:

administering to a human host an immunogenic response producing amount of a vaccine composition according to claim 6.

10. A method for protecting a human host against whooping cough which comprises:

administering to a human host an immunogenic response producing amount of a vaccine composition according to claim 8.

* * * * *